(12) United States Patent
Longest et al.

(10) Patent No.: US 12,582,783 B2
(45) Date of Patent: Mar. 24, 2026

(54) DRY POWDER INHALERS AND INTERFACES FOR IMPROVED AEROSOL DELIVERY TO CHILDREN

(71) Applicant: VIRGINIA COMMONWEALTH UNIVERSITY, Richmond, VA (US)

(72) Inventors: Worth Longest, Richmond, VA (US);
Dale Farkas, Richmond, VA (US);
Karl Bass, Richmond, VA (US);
Michael Hindle, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 746 days.

(21) Appl. No.: 17/794,660

(22) PCT Filed: Jan. 22, 2021

(86) PCT No.: PCT/US2021/014595
§ 371 (c)(1),
(2) Date: Jul. 22, 2022

(87) PCT Pub. No.: WO2021/150878
PCT Pub. Date: Jul. 29, 2021

(65) Prior Publication Data
US 2023/0173203 A1 Jun. 8, 2023

Related U.S. Application Data

(60) Provisional application No. 62/964,187, filed on Jan. 22, 2020.

(51) Int. Cl.
*A61M 15/00* (2006.01)

(52) U.S. Cl.
CPC .... *A61M 15/0021* (2014.02); *A61M 15/0086* (2013.01); *A61M 2202/064* (2013.01)

(58) Field of Classification Search
CPC .......... A61M 15/0021; A61M 15/0086; A61M 2202/064; A61M 11/06; A61M 15/0005; A61M 15/003; A61M 15/0033; A61M 2206/20; A61M 15/0043; A61M 2210/0618; A61M 11/02; A61M 2210/0625
See application file for complete search history.

(56) References Cited

U.S. PATENT DOCUMENTS

| | | | | |
|---|---|---|---|---|
| 5,676,130 | A * | 10/1997 | Gupte | A61M 11/002 |
| | | | | 128/200.14 |
| 5,724,959 | A * | 3/1998 | McAughey | A61M 11/002 |
| | | | | 128/203.15 |
| 6,715,485 | B1 | 4/2004 | Djupesland | |
| 2012/0298106 | A1* | 11/2012 | Kjellgren | A61M 15/0043 |
| | | | | 128/203.15 |
| 2013/0291866 | A1 | 11/2013 | Smutney et al. | |
| 2015/0107589 | A1* | 4/2015 | Longest | A61K 47/12 |
| | | | | 128/203.15 |

* cited by examiner

*Primary Examiner* — Elliot S Ruddie
(74) *Attorney, Agent, or Firm* — WCF IP

(57) ABSTRACT

Exemplary embodiments include dry powder inhalers (DPIs) and patient interfaces which improve delivery of aerosols to patients, especially children.

25 Claims, 8 Drawing Sheets

MP2

100

101

102

103

| POSITIVE PRESSURE AIR SOURCE | → | DPI (INCLUDING AEROSOLIZATION CHAMBER) | → | PATIENT INTERFACE |

133     135

131

134     136

134

132

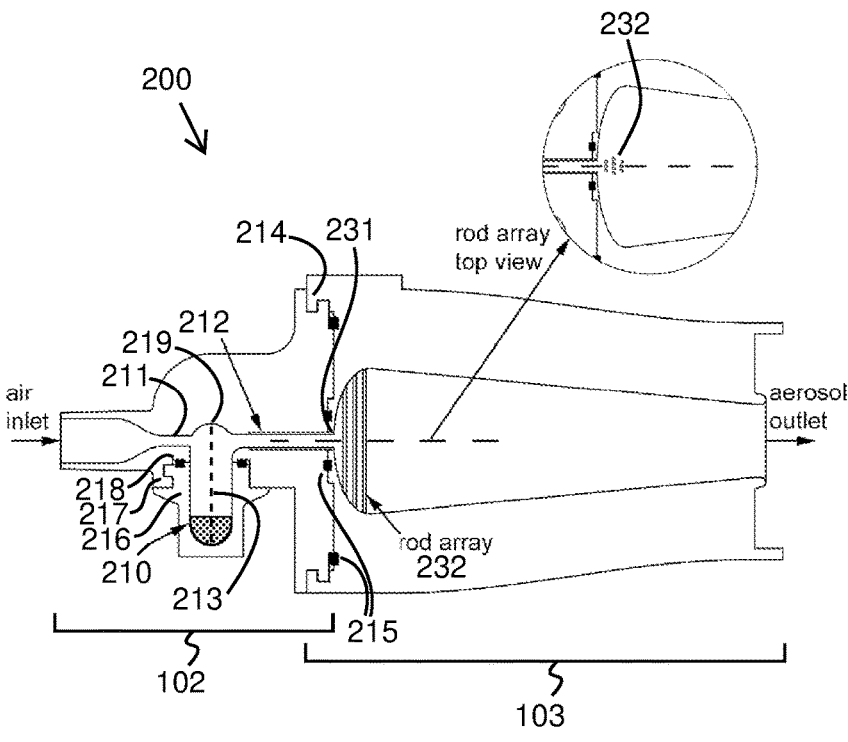
Figure 2A
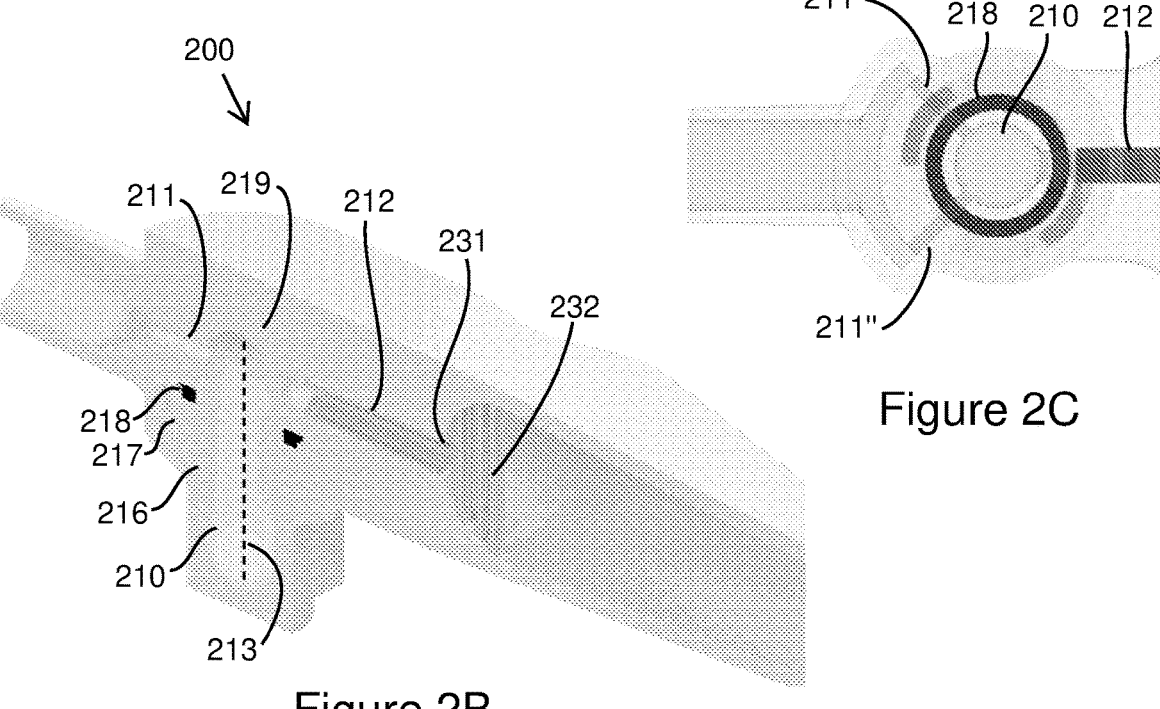
Figure 2B
Figure 2C

DRY POWDER INHALERS AND INTERFACES FOR IMPROVED AEROSOL DELIVERY TO CHILDREN

STATEMENT OF GOVERNMENT INTEREST

This invention was made with government support under Grant Numbers R01HD087339 and R01HL139673 awarded by the National Institutes of Health. The US government has certain rights in the invention.

FIELD OF THE INVENTION

The invention is generally related to dry powder inhalers (DPIs) and, in particular, to DPIs and related apparatuses configured to minimize depositional losses and provide exemplary delivery of aerosolized therapeutics to children.

BACKGROUND

While it is relatively well known that smaller particle size can significantly improve the delivery of pharmaceutical aerosols to infants and children, this approach has not been widely applied. Reasons that small particle aerosols may not commonly be used for pharmaceutical aerosol delivery to children include: (i) low dose delivery rates, (ii) difficulty in generating the small aerosol size, and (iii) high potential to exhale the dose. Dry powder inhalers can frequently be used to rapidly generate and deliver high aerosol doses, but typically have a relatively large apparent aerosol diameter with high extrathoracic losses. Weers, Jeffry G., et al. "Idealhalers versus realhalers: is it possible to bypass deposition in the upper respiratory tract?." Journal of aerosol medicine and pulmonary drug delivery 32.2 (2019): 55-69. DPIs typically employ high turbulence and small diameter flow passages leading to the mouth-throat region in order to deaggregate dry powder formulations and form an inhalable aerosol. While some inhalable dose fraction can be formed with this method, depositional losses in the device and mouth-throat (MT) region are typically high due to increased impaction deposition and turbulence dispersion.

SUMMARY

As described in this disclosure, a positive-pressure air-jet DPI with a spray-dried powder formulation effectively generates a small aerosol size (approximately 1.7 μm). The device actuation speed is fast (<5 s), resulting in a high dose delivery rate. Furthermore, an excipient enhanced growth (EEG) particle formulation may be used to reduce the potential for exhalation of the spray-dried aerosol and to enable targeted drug delivery (see, e.g., U.S. Pat. No. 10,105,500, issued Oct. 23, 2018, incorporated herein by reference.)

The vast majority of DPIs on the market are passive devices, which form an aerosol under negative pressure in response to a user's inhalation through the device. In contrast, exemplary embodiments herein use active devices. Active devices use an energy source external to the user to form the aerosol. Positive-pressure active devices implement an external gas source to aerosolize the powder, which can be supplied by an air-syringe, manual ventilation bag, or compressed air electromechanical system. Depending on the volume of gas used, these DPIs can be classified as high (>200 ml) or low (<200 ml) actuation air-volume (AAV) devices.

Considering dry powder aerosol delivery to pediatric subjects, positive-pressure DPIs that deliver the aerosol and a full inhalation breath overcome a number of previously observed limitations. First, use of a consistent positive-pressure gas source to form and deliver the aerosol significantly reduces inter and intra-subject variability in drug delivery, especially if extrathoracic depositional loss can also be reduced. Secondly, positive-pressure operation provides the option of oral or nasal lung delivery of the aerosol. Potential advantages of trans-nasal delivery include administering pharmaceutical aerosol to infants and children that are too young to use a mouthpiece (approximately 2-3 years old) and the ability to treat the nasal and lung airways simultaneously. Thirdly, positive-pressure gas delivery will expand rather than collapse the extrathoracic airways, which should improve lung delivery of the aerosol. Providing a known volume of gas delivery can be used to assist with deep lung inhalation and expansion of constricted or obstructed tracheobronchial airways, thereby enabling improved targeting of the deep lung regions and delivery to diseased airways. Finally, positive pressure aerosol delivery requires forming a sealed connection with the lungs via the extrathoracic region. This sealed system prevents the user from exhaling through the powder containment region, which can degrade powder performance, and can be used to encourage a brief breath-hold to improve lung retention of the aerosol.

Some exemplary embodiments disclosed herein include a positive-pressure air-jet dry powder inhaler (DPI) for efficient aerosol generation and delivery to adults, children, and infants. The exemplary air-jet DPI implements a small diameter inlet airflow passage, aerosolization chamber, and small diameter outlet aerosol flow passage. Using this approach, actuation air-volume devices (AAVs) of 10 ml and lower have been shown to effectively aerosolize 10 mg powder masses in devices that were designed to be integrated with a ventilation system, which required a small AAV so as to not increase the ventilation volume.

For pediatric drug delivery, a positive-pressure pediatric air-jet DPI is disclosed that is operable with a ventilation bag or compressed gas supply with e.g. 750 ml of air, in order to aerosolize a powder and provide a full inhaled breath for a child. The AAV selected for 5-year-old children was based on adult inhalers typically being tested at 50-75% of total lung capacity (TLC). For a 5-year-old child, typical TLC is 1.55 L, such that the 750 ml AAV is at the lower end of the 50-75% TLC range used for adults. Using a highly dispersible spray-dried formulation (Son, Longest, Tian, & Hindle, 2013), the best case pediatric air-jet DPI produced an aerosol MMAD<1.75 μm and a fine particle fraction (<5 μm)≥90% based on emitted dose. Actuation with the ventilation bag enabled lung delivery efficiency through the nasal and oral interfaces to a tracheal filter of 60% or greater, based on loaded dose. In both oral and nose-to-lung administrations, extrathoracic depositional losses were <10%.

Computational fluid dynamics (CFD) studies of aerosolization within exemplary air-jet DPIs have revealed some interesting characteristics. At both high and low AAVs, increasing turbulence increases emitted dose (which is advantageous), but also increases MMAD (which is typically detrimental for efficient lung delivery). The direct relationship between internal device turbulence and MMAD is a unique characteristic of the air-jet system as most other aerosol generation units are assumed to have the opposite behavior. This behavior was attributed to a two stage aerosolization process of initial fluidization of the powder followed by turbulent deaggregation of fluidized agglomerates. Excess turbulence is viewed to fluidize the powder too rapidly leaving less time for secondary turbulent deaggregation. Provided that sufficient emitted dose can be maintained, an exemplary air-jet DPI therefore performs better with lower flows and less turbulence, which are ideal characteristics for efficient aerosol administration to infants and children. Furthermore, devices tend to produce a direct linear relationship between emitted dose and MMAD, i.e., higher emitted dose is directly proportional to higher MMAD. CFD and in vitro aerosol characterization examples herein identify device configurations with beneficial emitted dose and MMAD relationships.

Within exemplary DPIs disclosed herein, different structures and airflow passage designs are implemented to generate the turbulence and particle aggregate break-up mechanisms that are needed to deaggregate the powder. Primary powder breakup and aerosolization occurs in the air-jet DPI (aerosolization chamber and outlet capillary). For a set amount of input energy (applied as a pressure drop across the device, positive or negative) a 3D rod array with unidirectional rods is also instrumental at aerosolizing the powder, as contrasted with a standard constricted tube, impaction surface, 2D mesh, and inward radial jets. The rod array may be added to provide a secondary mechanism of aerosol breakup, further reducing the aerosol size with negligible depositional loss. The rod array also functions to break apart the turbulent jet reducing downstream aerosol impaction and depositional loss on the way to the lungs.

While exemplary air-jet DPIs disclosed herein improved MMAD with lower internal turbulence, a potential disadvantage is the small diameter jet of high velocity aerosol exiting the DPI which can lead to unnecessary impaction loss in the patient interface and extrathoracic airways. To reduce the effect of the high-intensity turbulent jet that exits the air-jet DPI, exemplary pediatric patient interfaces are disclosed which are arranged in the aerosol pathway between the DPI and patient. Internal structures within the interface may include one or more of non-smooth surfaces, rapid and stepped expansions, impaction surfaces and various 3D rod array designs.

CFD results presented in Example 1 show that a combination of a 3D rod array with a rapidly expanding interface in the region of the rod array best dissipates the turbulent jet from the DPI while minimizing depositional loss in the mouthpiece. For oral aerosol administration, the optimal flow passage compared with previous design candidates reduces device, mouthpiece, and mouth-throat depositional losses by factors of 8-, 3-, and 2-fold, respectively, which results in a significant increase in lung delivery efficiency. For nose-to-lung aerosol administration, the optimal flow pathway compared with previous designs reduced device, nasal cannula, and nose-throat depositional losses by 16-, 6-, and 1.3-fold, respectively.

Example 2 considers pediatric oral aerosol delivery with a realistic in vitro MT airway model using an air-jet DPI and MP interface which included a 3D rod array to improve secondary break-up of the aerosol and dissipate the turbulent jet before entering the MT region. A vertical aerosolization chamber is employed which is less sensitive to larger powder mass loadings. Devices were loaded with 10 mg doses of a spray dried formulation and actuated with positive pressure using a flow rate of 10-20 L/min and an air volume of 750 ml consistent with a 5-year-old child. Inclusion of the 3D rod array in the MP was shown to further reduce the aerosol size to an MMAD of <1.7 μm without significantly increasing aerosol loss in the device. Best case device and MP combinations produced <2% MT depositional loss and

4

>70% lung delivery efficiency (based on loaded dose) in a realistic in vitro pediatric MT geometry.

Some embodiments include a nasal interface in place of an oral interface that includes a 3D rod array to enable high efficiency nose-to-lung aerosol administration to subjects that are too young to use a mouthpiece.

According to an aspect of some embodiments, an air jet dry powder inhaler (DPI) system comprises an air jet DPI and a patient interface. An exemplary air jet DPI comprises a fixed position elongate aerosolization chamber with a longitudinal axis; one or more inlets for forming at least one cross flow air jet with an air jet axis, and one or more outlets leading off the aerosolization chamber. The air jet axis is at a non-zero angle with the longitudinal axis of the aerosolization chamber. An exemplary patient interface comprises a lumen with one or more exit orifices, at least one inlet for delivering an aerosol air jet to the lumen from the one or more outlets leading off the aerosolization chamber, and a 3D rod array arranged in the lumen such that the aerosol jet exiting the at least one inlet must pass through the 3D rod array to reach the one or more exit orifices.

An exemplary 3D rod array comprises a plurality of rows of rods which extend between opposite walls of the lumen. The 3D rod array may span an entire cross-sectional distance of the lumen between the at least one inlet and the one or more exit orifices in a direction perpendicular to a long axis of the rods of the 3D rod array. Alternatively, the 3D rod array may span less than an entire cross-sectional distance (e.g., 50% or less, 30% or less, 15% or less, 5% or less) of the lumen between the at least one inlet and the one or more exit orifices in a direction perpendicular to a long axis of the rods of the 3D rod array. At least one gap between a wall of the lumen and a rod of the 3D rod array nearest the wall may exceed a maximum distance between any two adjacent rods. An exemplary 3D rod array is spaced 0 to 5 mm away from the at least one inlet orifice along a primary flow axis of the lumen. The 3D rod array may be spaced 1 to 2 mm away from the at least one inlet along the primary flow axis of the lumen. At least one cross-sectional dimension of the lumen may increase along a long axis of the lumen in a direction away from the at least one inlet for a length of the long axis corresponding in position with the 3D rod array. The at least one cross-sectional dimension of the lumen is oriented perpendicular to a long axis of the rods of the 3D rod array. The increase in the at least one cross-sectional dimension may begin at or before the at least one inlet along a long axis of the lumen in a direction toward the one or more outlet orifices. The increase may be gradual or instantaneous. At least one inlet may comprise a flow passage that projects a non-zero distance into the lumen from one end of the lumen opposite the one or more exit orifices before admitting the air jet to the lumen.

An exemplary method of administering a drug to a patient may comprise aerosolizing the drug in a vertical aerosolization chamber before forming an aerosol jet and forcing the aerosol jet through a 3D rod array before the aerosol reaches the patient.

According to aspects of some exemplary air jet DPIs, the air jet axis is perpendicular to the longitudinal axis of the aerosolization chamber. The longitudinal axis of the aerosolization chamber has a vertical orientation in a state of use. At least one of the one or more inlets is aligned on a common axis with at least one of the one or more outlets. The air jet axis passes only through an upper longitudinal segment of the aerosolization chamber. The one or more inlets and the one or more outlets are all positioned at an upper longitudinal segment of the aerosolization chamber. The upper longitudinal segment may extend no more than 50% of a length (or 25% of the length) of the aerosolization chamber. A lower longitudinal segment of the aerosolization chamber is removable and reattachable to the upper longitudinal segment. The lower longitudinal segment is opposite the upper longitudinal segment. The lower longitudinal segment of the aerosolization chamber may be configured to accommodate a fractional part of a Size 0 capsule containing powder. The lower longitudinal segment of the aerosolization chamber may be configured to contain powder that is not in a capsule. The lower longitudinal segment of the aerosolization chamber may be open or openable to an environment and configured to receive a containment unit holding a powder. The containment unit may be reusable or disposable.

BRIEF DESCRIPTION OF THE DRAWINGS

FIG. 2A illustrates the inner flow pathway of an exemplary air-jet DPI connected to an exemplary patient interface for oral inhalation.

FIG. 2B is a cross-sectional three-dimensional view of the air-jet DPI and patient interface of FIG. 2A.

FIG. 2C is a top view of an alternative DPI arrangement which has multiple inlet capillaries.

DETAILED DESCRIPTION

Figure 1A:
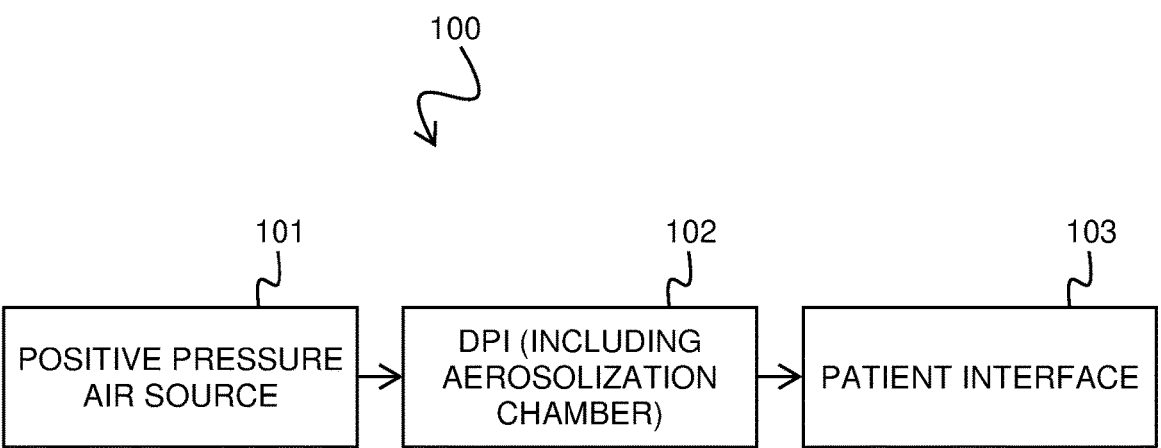
FIG. 1A is an overview of flow passages for an exemplary air-jet dry powder inhaler (DPI) system 100.

FIG. 1A shows an overview of flow passages for an exemplary pediatric air-jet DPI system 100 for both oral and nasal aerosol administration. Three main subparts illustrated are a positive pressure air source 101, a dry powder inhaler (DPI) 102 which includes an aerosolization chamber, and a patient interface 103. It will be understood to those of ordinary skill in the art that all three of these elements are typically involved in a patient's treatment according to exemplary embodiments. As a semantic matter, however, the term "DPI system" or simply "system" may be used herein to refer to all three elements collectively or any one or pair of the elements 101, 102, and 103. An exemplary DPI system may also include further elements not represented by the blocks in FIG. 1A.

Figures 1B, 1C:
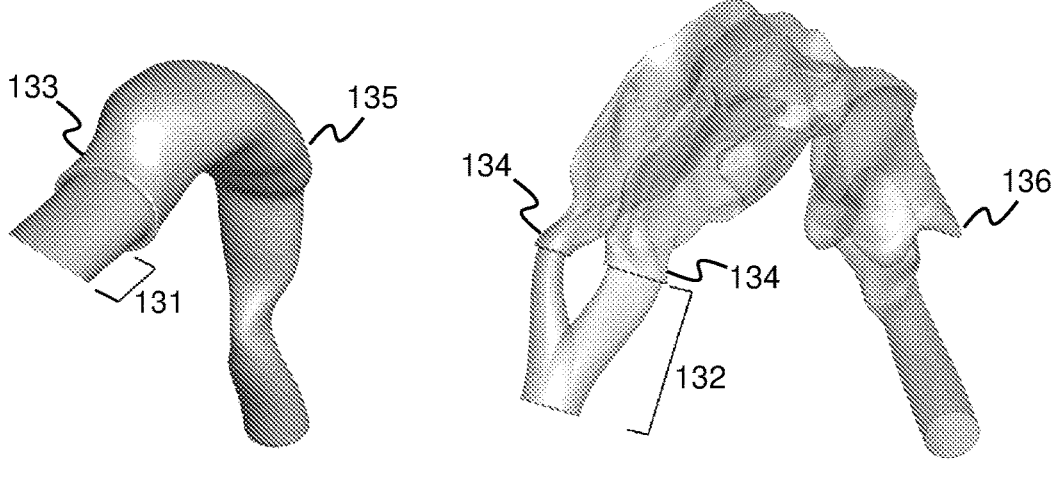
FIG. 1B shows the distal end of a patient interface for oral administration.
FIG. 1C shows the distal ends of a patient interface for intranasal administration.

FIG. 1B shows a distal end 131 of a patient interface 103 configured for mouth-throat 135 aerosol administration to the patient's lungs. The distal end 131 of the patient interface 103 is configured to form a seal with the patient's mouth 133. FIG. 1C shows an alternative distal end 132 of the patient interface 103 configured for nose-throat 136 aerosol administration to the patient's lungs. The distal end 132 comprises a cannula bifurcation and is configured to form a seal with the patient's nostrils 134. It should be appreciated that many exemplary embodiments herein are configured for optimal delivery of aerosol to the lungs, in contrast to the nose. Aerosol is desirably passed through the mouth-throat or nose-throat with minimal deposition until it reaches the lungs.

FIGS. 2A and 2B show the combined assembly 200 of an exemplary dry powder inhaler (DPI) 102 and patient interface 103. The two parts 102 and 103 may be configured to be attachable to and separable from one another with a twist-lock or other attachment mechanism 214. The attachment mechanism 214 may include one or more silicone o-rings 215 to form a tight seal through which aerosol may not escape. Within the DPI 102 an exemplary aerosolization chamber 210 comprises or else adjoins an inlet orifice flow passage 211 and an outlet orifice flow passage 212. The inlet and outlet orifice flow passages 211 and 212 may be constructed with hollow metal capillaries and are often referred to as inlet and outlet capillaries, whether or not the passages are made of metal or another suitable material. The inlet and outlet capillaries may be oriented along the long/longitudinal axis 213 of the aerosolization chamber 210 or at a non-zero angle with the longitudinal axis 213, e.g., perpendicular as discussed below and illustrated in FIGS. 2A and 2B. The inlet and outlet capillaries are typically but not always necessarily aligned on the same axis as one another. The linear air jet does not impinge on the initial bed of powder. Rather, secondary velocities in the aerosolization chamber form the aerosol from the dry powder bed. The perpendicular/vertical orientation of the aerosolization chamber can accommodate higher powder masses and proves easier to load than alternatives such as a horizontal aerosolization chamber. A vertical aerosolization chamber is less sensitive to larger powder mass loadings. A bypass flow may or may not be included as well.

Exemplary capillary and orifice diameters are 1.3 to 3.5 mm. Exemplary flow rates of air are 5 to 30 LPM for children, or in a range of 10 to 45 LPM for adults. Exemplary pressure drops across the system 100 is 1.5 to 6 kPa or higher. Exemplary actuation flow volumes are 100 ml to 1.5 L or higher.

The vertical aerosolization chamber is a fixed position chamber, that is to say it does not involve oscillation or spinning. The vertical aerosolization chamber 210 may be configured consistent with the volume and shape of a Size 0 capsule, though the volume and shape may vary among embodiments to accommodate other dry powder capsule volumes. With the size matching of chamber and capsule, the capsule does not oscillate or spin based on the fixed position configuration. The chamber 210 permits loading of whole capsules or less than whole capsules. For example, the chamber 210 is configured to enable loading of a half or three-quarter capsule unit with powder. Partial capsule design contains an attached ring near the open end of the capsule that enables foil sealing and connection to the device. A partial capsule (e.g. half capsule) containing a powder may be secured in the DPI aerosolization chamber separately or inserted into a lower unit that aids with twist seal closure. The vertical orientation of axis 213 when the system 100 is in use also permits dry powder to be inserted directly into the aerosolization chamber 210 with ease and without reliance upon the powder's containment in a capsule. A bottom portion 216, which may be referred to as a containment unit in reference to its containment of the dry powder bed prior to aerosolization, may unscrew from a complementary top portion 219 via a reversable attachment mechanism 217 such as threaded screws or one or more magnets. The attachment mechanism 217 may include one or more silicone o-rings 218 to provide a seal between the bottom 216 and top 219 portions of the aerosolization chamber 210.

The vertical orientation of the capsule chamber offers multiple advantages including (i) improved ease of loading and safety for pediatric use, (ii) ability to use existing capsule filling technology and equipment in manufacturing of doses, and (iii) improved performance in powder aerosolization. Regarding ease of loading and safety, other air-jet designs require separation of the device along a midplane and insertion of a capsule that is pierced by sharp capillaries. While these capillaries may be recessed, they may provide some risk of injury. Furthermore, capsule piercing in DPIs is known to be variable and imprecise. In contrast, attachment of element 216 of FIG. 2A is expected to be easier for device loading. Loading strategies also enable the removal of a foil covering instead of capsule piercing, which may be viewed as safer.

Figure 2D:
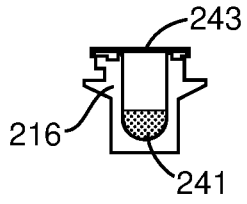
FIG. 2D is a dose loading embodiment in which a containment unit is preloaded with powder.
Figure 2E:
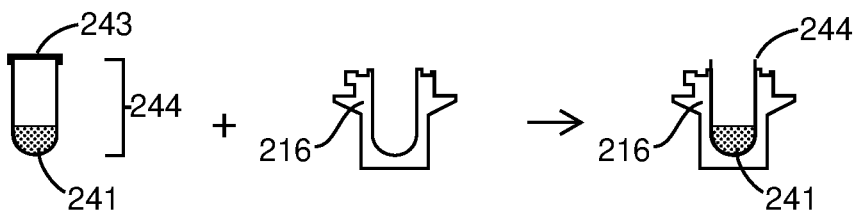
FIG. 2E is a dose loading embodiment in which a partial capsule is unsealed and then loaded into a containment unit.
Figure 2F:
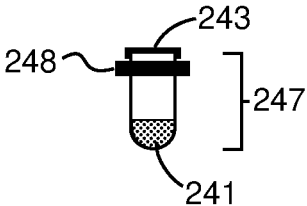
FIG. 2F is a dose loading embodiment in which a customized partial capsule is unsealed and then used directly as the DPI containment unit.

FIGS. 2D, 2E, and 2F show non-limiting examples for dose loading of the device 200. Attachment of element 216 provides a highly reproducible aerosolization chamber in contrast with capsule piercing. The vertical orientation and loading strategies enable the use and filling of partial capsule bodies, e.g., base ½ or ¾ components of a Size 0 capsule. This is advantageous from a dose manufacturing and filling perspective in that existing capsule-oriented equipment and technology can be utilized with the addition of a seal (e.g., foil seal) on the top of the capsule.

FIG. 2D is a dose loading embodiment in which a containment unit 216 is preloaded (e.g., by a manufacturer as opposed to an end user) with powder 241 and capped with a cover 243 such as foil seal. The containment unit 216 supplants the traditional containment role of a disposable Size 0 capsule. The shape of the containment unit 216 may but is not necessarily required to approximate a fractional part (e.g., two-thirds or three-quarters) of a capsule shape, the remaining fractional part of the total shape of a Size 0 capsule being supplied by the top portion 219 of the aerosolization chamber 210. Immediately prior to use, a user simply removes the cover 243 of foil and installs the containment unit 216 using the attachment mechanism 217 as discussed above. After actuation of the air-jet DPI, the now substantially empty containment unit 216 may be disposed of or recycled.

FIG. 2E is another dose loading embodiment. In this case, a partial capsule such as a three-quarter piece of a traditional Size 0 capsule 244 is preloaded with powder 241 and capped with a cover 243 such as a foil seal. Immediately prior to use, a user simply removes the cover 243 of foil and installs the now opened capsule 244 into the containment unit 216. The containment unit 216 is then connected to the remainder of the air-jet DPI using attachment mechanism 217. After actuation of the air-jet DPI, the empty capsule 244 may be disposed of and the substantially empty containment unit 216 may be reused, disposed of, or recycled.

FIG. 2F is still another dose loading embodiment. In this case, a modified capsule 247 which may be approximately ¾ of a conventional Size 0 capsule is preloaded with powder and capped with a cover 243. Here the capsule 247 serves as the containment unit 216. An inexpensive connector 248 e.g. a plastic ring is connectable with a remainder of the attachment mechanism 217 necessary to temporarily but in an airtight fashion attach the capsule 247 to the top portion 219 of the aerosolization chamber after the cover 243 is removed just before use. Once emptied the capsule 247 including the connector 248 may be disposed.

Air-jet DPI performance is significantly improved when the inlet jet does not strike the initial powder bed in the orientation of use. The vertical aerosolization chamber orientation allows a significant portion of the aerosol chamber to be filled with powder, thereby maximizing space usage within the dose containment unit, which is critical for high dose powder operation. This portion of preloaded powder in the vertical orientation without jet impaction can be 50 to 100% larger than for a capsule in the horizontal orientation with the same volume. While the inlet and outlet air jets can cross the aerosolization chamber at any location provided the jet does not impinge on the powder bed, dose storage and loading are maximized by implementing these structures at the top (preferably upper ¼) of the air-jet DPI when in the orientation of intended use.

FIG. 2C is a top view of an alternative DPI arrangement which has multiple inlet capillaries 211' to the aerosolization chamber 210. The o-ring 218 and outlet capillary 212 are the same as in FIGS. 2A and 2B.

The diameters of the flow passages 211 and 212 (together with the delivered air flow rate) control the strength of the high-speed jet of air within the aerosolization chamber 210 and the release characteristics of the aerosol from the DPI 102. Positive-pressure gas passes through the inlet airflow passage 211 and forms a high-speed turbulent jet within the aerosolization chamber 210. Secondary flow velocities formed by the high-speed jet are used to initially fluidize the powder. As the fluidized powder enters the high speed jet region, additional powder deaggregation occurs. The small diameter outlet orifice serves to both help form the secondary velocities and allow passage of sufficiently deaggregated particles out of the aerosolization chamber 210. As mentioned above, the outlet flow passage 212 may be constructed with a stainless steel hollow capillary that has been shown to produce minimal depositional internal loss. The outlet flow passage 212 is connected to the patient (mouth or nose) by the patient interface 103. The DPI outlet flow passage 212 creates a high speed air jet leaving the DPI 102 due to its diameter. Were such high speed air jet directly administered to the patient, such as with a patient interface that is no more than a simple tubular conduit of constant diameter, it can induce unnecessarily high depositional losses in both the patient interface and extrathoracic airways.

As depicted in FIGS. 2A and 2B, an inlet 231 of the patient interface 103 passes the high speed air jet leaving the DPI 102 and containing the aerosol through a 3D rod array 232, with the rods in a parallel staggered arrangement, as depicted in the top view inset of FIG. 2A. The 3D rod array 232 may comprise some features described by U.S. Pat. No. 10,105,500 B2 which is incorporated herein by reference. The purpose of the 3D rod array is two-fold. First, the 3D rod array is configured to disaggregate an aerosol for a given amount of input energy and with minimal depositional loss. As a result, the 3D rod array reduces the aerosol size. Secondly, the 3D rod array effectively dissipates a turbulent jet, thereby minimizing downstream deposition including depositional loss on the rods and on the back of the throat. Deposition can arise from both turbulent dispersion and impaction. The 3D rod array creates a nearly uniform flow leaving the patient interface 103. The 3D rod array breaks the high velocity isosurface and largely eliminates its presence in the patient interface 103.

The patient interface 103, especially when configured as a mouthpiece (with delivery of the aerosol through the patient's mouth instead of through the nose), comprises a smooth expansion of the sidewalls in the longitudinal direction of the patient interface 103, from at or near the orifice 231 to the end or past the longitudinal position at which the 3D rod array 232 ends. The widening cross-section of the patient interface 103 in the vicinity of the rods minimizes or avoids depositional loss on the sidewalls. Said differently, expanding the sidewalls in the vicinity of the 3D rod array and in the direction of jet dispersion maintains low deposition in the patient interface. Generally, the at least temporary widening (expansion) of the patient interface in exemplary embodiments may be described as follows. In a direction at a right angle to the rod length, the mouthpiece (MP) or other patient interface should rapidly expand to at least 3.6 cm (diameter of elliptical major axis) at a flow rate of up to 13.3 LPM. In testing, expansion reduced the total MP and MT depositional loss by a factor of 0.6 (8.7% vs. 14.6%) compared with a 0.9 cm expansion (data pertained to FIG. 8 embodiments, RE-a & RA-a vs. RE-d & RA-a). At higher flow rates more expansion is likely necessary. At lower flow rates less expansion may be acceptable.

To further describe the interface expansion in the vicinity of a partial rod array, consider the partial rod array 232 shown in FIG. 2A viewed from above in the inset image. In this embodiment, the interface sidewalls are expanded in a direction at a right angle to the rods such that the rod array occupies approximately 15% of the linear distance and open space without the rod array occupies 85% of the linear distance to the wall. The percentage of linear distance to the interface side-wall occupied by the rod array may be 5-50%, more preferentially, 10-30%, more preferentially approximately 15%.

Exemplary 3D rod arrays may, but need not necessarily, extend across the entire width of the patient interface in all embodiments. According to the exemplary embodiment shown in FIGS. 2A and 2B, a small rod array with a 3-4-3 pattern is used directly at the orifice 231 of the small diameter flow pathway leading out of the air-jet DPI 102, without the complexity and expense of additional rods. More generally, rod arrays in patient interfaces may fit into either of at least two categories of embodiments. In the first category, or which the configuration may sometimes be called a full array, the rod array extends all the way across the interface, from wall-to-wall, ceiling-to-floor so to speak. In order for aerosol to reach the outlet of the patient interface, it inevitably must pass between two rods or else a similarly sized gap between the rod nearest a sidewall. In this category a comparatively large number of rods are needed, but a resulting advantage is that spacing between the capillary outlet (leading from the air-jet DPI) and rod array becomes less significant a control variable and can be larger or smaller as desired to reduce manufacturing costs.

In the second category, for which the configuration may sometimes be called a partial array, a small rod array is used very close to the capillary outlet. The distance between and among rods is very small compared to the gaps between sidewalls and the nearest rods. The proximity of the capillary outlet to the first row of rods must be such that the jet of aerosol leaving the capillary outlet is forced to flow through the rod array and prevented from merely flowing around the rod array at the predetermined flow rate(s) for which the device is configured for use. The distance from the capillary outlet to the nearest row of rods may be 0 to 5 mm, generally better at 1 to 2 mm, with an exemplary distance being 1.25 mm. This second category is often preferred because of the cost of rod production as far fewer rods are needed compared to the first category of devices. However rapid expansion in at least one dimension—specifically that which is perpendicular to the long axis of the rods—is generally needed for the second category of devices. As described above, the linear distance of the expansion in the vicinity of the rods as viewed in FIG. 2A from above (inset with 232) between the centerline and interface sidewall is preferentially occupied by 15% rod array and 85% open area.

Rod arrays may come in different dimensions for different embodiments. For the sake of non-limiting illustration, however, the following are some exemplary dimensional measures. Inlet capillary diameter may be 2.39 mm. Rod diameter may be 0.5 mm or smaller. All rods may have the same diameter or, in some cases, some rods may differ in diameter from other rods. Exemplary ranges in terms of capillary diameters are 1.25 mm to 7.5 mm for the second category discussed in the preceding paragraph (based on total losses of 14.6 to 19.0 for RE-a & RA-a and RE-a & RA-c, see FIG. 8); 1.25 mm to 21.25 mm for a full array (based on total losses of 13.1 to 14.4 for CE & RA-d/e/f, again see FIG. 8). The rod centerline spacing may be 1.75 mm in the streamwise direction; 1.00 mm perpendicular to the bulk flow. The distance from capillary outlet to first row of rods may be 1.25 mm. The mouthpiece (MP) internal ellipse dimensions (as diameters) at flared base may be 36 mm×26 mm. The mouthpiece (MP) internal ellipse dimensions (as diameters) at outlet to patient may be 18 mm×13 mm.

Generally, a 3D rod array may be characterized by a plurality of rows each of which has a plurality of unidirectional rods disposed within a flow passage of an inhaler and spaced apart along a primary direction of air flow in the flow passage. A primary direction of air flow in the flow passage may be described as a longitudinal direction or z-direction of the flow passage. Successive unidirectional rows in a primary direction of air flow may or may not lie on the same line and are preferably staggered. This generally means that the rods of a first row in a first x-y plane of the flow passage and the rods of a second row in a second x-y plane of the flow passage are not in direct alignment with each other in the z-direction. The rows are preferably parallel to one other, and the rods are generally parallel to one another. In a preferred embodiment the rods in the second x-y plane are offset by 1-99% (most preferably 50%) from the rods in the first x-y plane such that air flowing (generally with increased velocity) between two rods of the first row in the first plane impacts on one or more rods (preferably the centers of the rods) of the second row in the second plane. In a preferred embodiment, all the rods of the plurality of rows of a 3D rod array are oriented in a same direction. The FIG. 2A inset provides a cross-sectional view of an exemplary embodiment of a 3D rod array wherein there are three rows of rods and each successive row is offset by 50% from the preceding row such that air flowing between two rods impacts on the center of a rod in a subsequent row. Rod diameters are typically 0.5 mm or less to ensure low depositional loss of the aerosol.

FIGS. 3A-3C, 4A-4C, 5A-5C, 6A-6C, and FIG. 7 show four alternative embodiments for exemplary patient interfaces. The figures organized in groups of three show a top view, a side view, and an enlarged partial top view of a starting section of the lumen of the patient interface. Experimental evaluation of all four variants is discussed in Example 1 below.

Figures 3A, 3B, 3C, 4A, 4B, 4C:
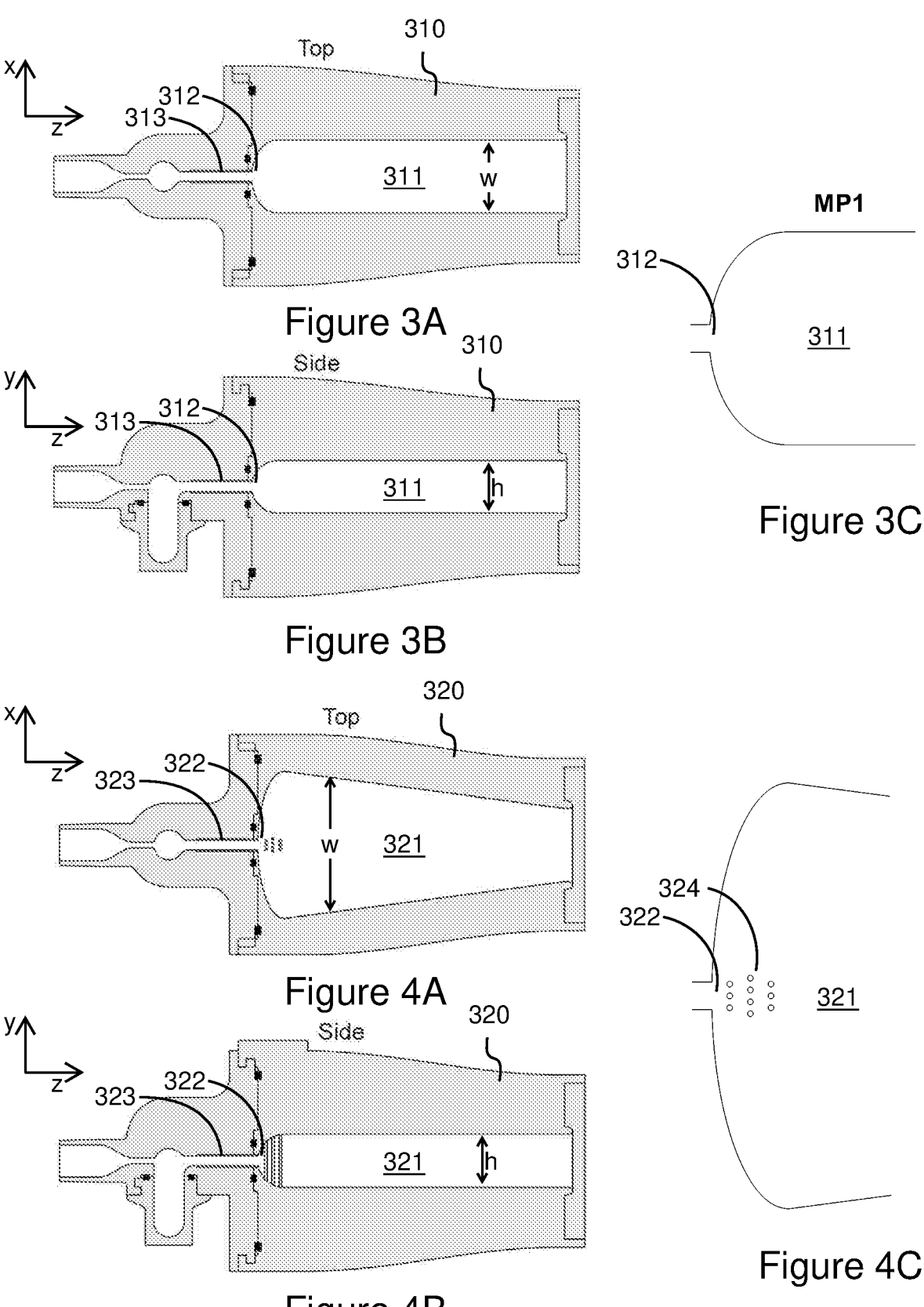
FIGS. 3A, 3B, and 3C show one embodiment of a mouthpiece.
FIGS. 4A, 4B, and 4C show a second embodiment of a mouthpiece.

FIGS. 3A and 3B show, respectively, a top view and a side view of a patient interface 310 which is a mouthpiece (MP). The lumen 311 of the patient interface 310 has an oval cross-section. The patient interface 310 provides rapid expansion of the MP wall beginning immediately but not before the outlet orifice 312 of the capillary 313, moving the surfaces available for deposition away from the aerosol and reducing losses. However, there is no mechanism to diffuse the high-velocity jet exiting the orifice 312.

FIGS. 4A and 4B show, respectively, a top view and a side view of a patient interface 320 which is a mouthpiece (MP). The patient interface 320 provides rapid expansion of the MP wall beginning immediately but not before the outlet orifice 322 of the capillary 323, moving the surfaces available for deposition away from the aerosol and reducing losses. The lumen 321 of the patient interface 320 has a cross-section which, along the z-axis after a 3D rod array, has a constant size in the y-dimension but which progressively reduces in size in the x-dimension. Moreover, the expansion of lumen 321 in the x-dimension is roughly twice the expansion of lumen 311. Adjacent to the orifice 322 is a 3D rod array 324.

Figures 5A, 5B, 5C, 6A, 6B, 6C:
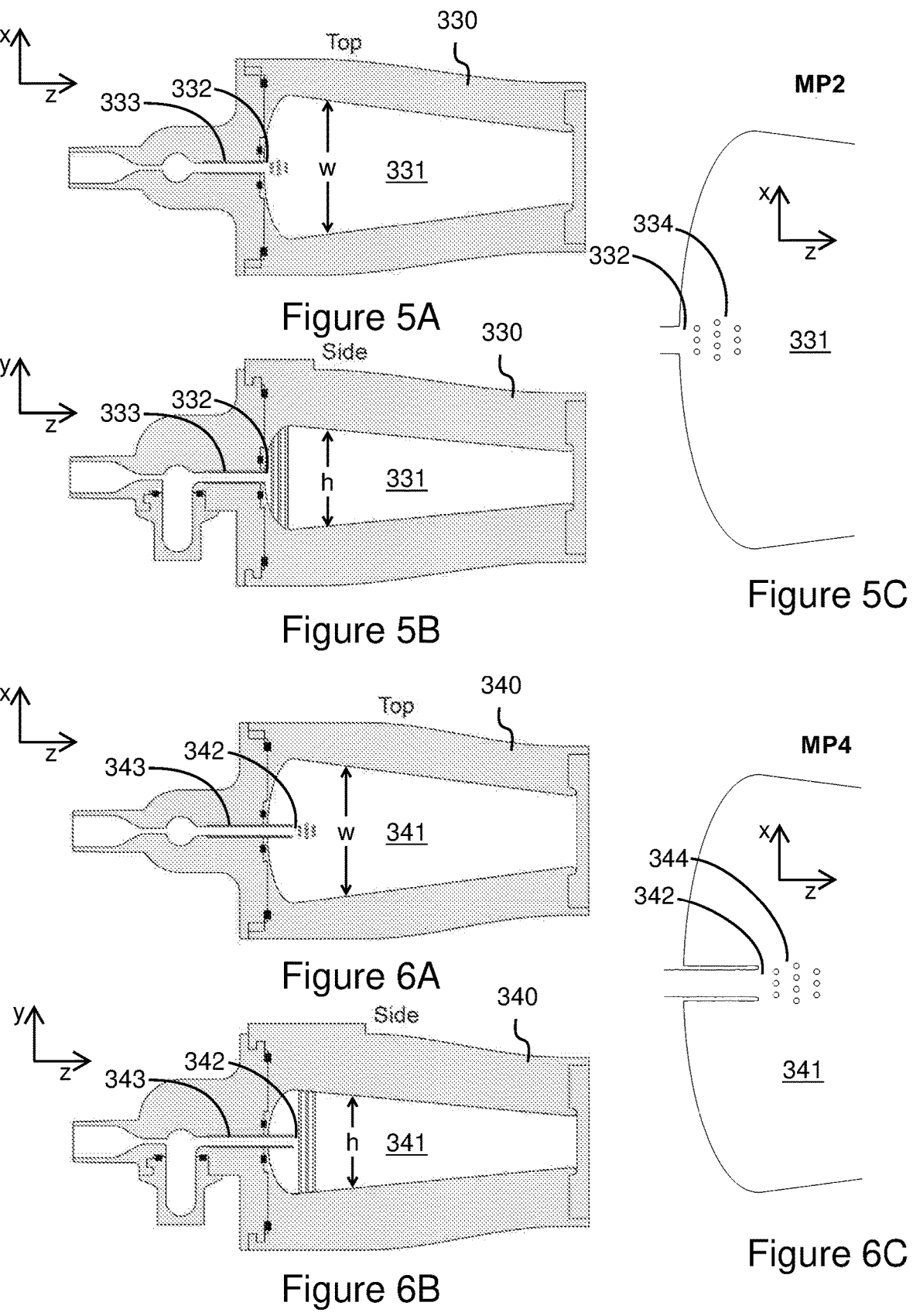
FIGS. 5A, 5B, and 5C show a third embodiment of a mouthpiece.
FIGS. 6A, 6B, and 6C show a fourth embodiment of a mouthpiece.

FIGS. 5A and 5B show, respectively, a top view and a side view of a patient interface 330 which is a mouthpiece (MP). The patient interface 330 provides rapid expansion of the MP wall beginning immediately but not before the outlet orifice 332 of the capillary 333, moving the surfaces available for deposition away from the aerosol and reducing losses. The patient interface 330 comprises a 3-4-3 configuration 3D rod array 334 to diffuse the high-velocity jet and reduce downstream aerosol losses.

FIGS. 6A and 6B show, respectively, a top view and a side view of a patient interface 340 which is a mouthpiece (MP). In contrast the patient interfaces 310, 320, and 330 discussed above, the patient interface 340 provides rapid expansion of the MP wall at a z-axis position that precedes the outlet orifice 342 of the capillary 343, moving the surfaces available for deposition away from the aerosol and reducing losses. The patient interface 340 extends the capillary 343 6 mm into the lumen 341 to both keep the aerosol away from wall surfaces and direct the high-velocity jet through the 3D rod array 344.

Figures 7, 8:
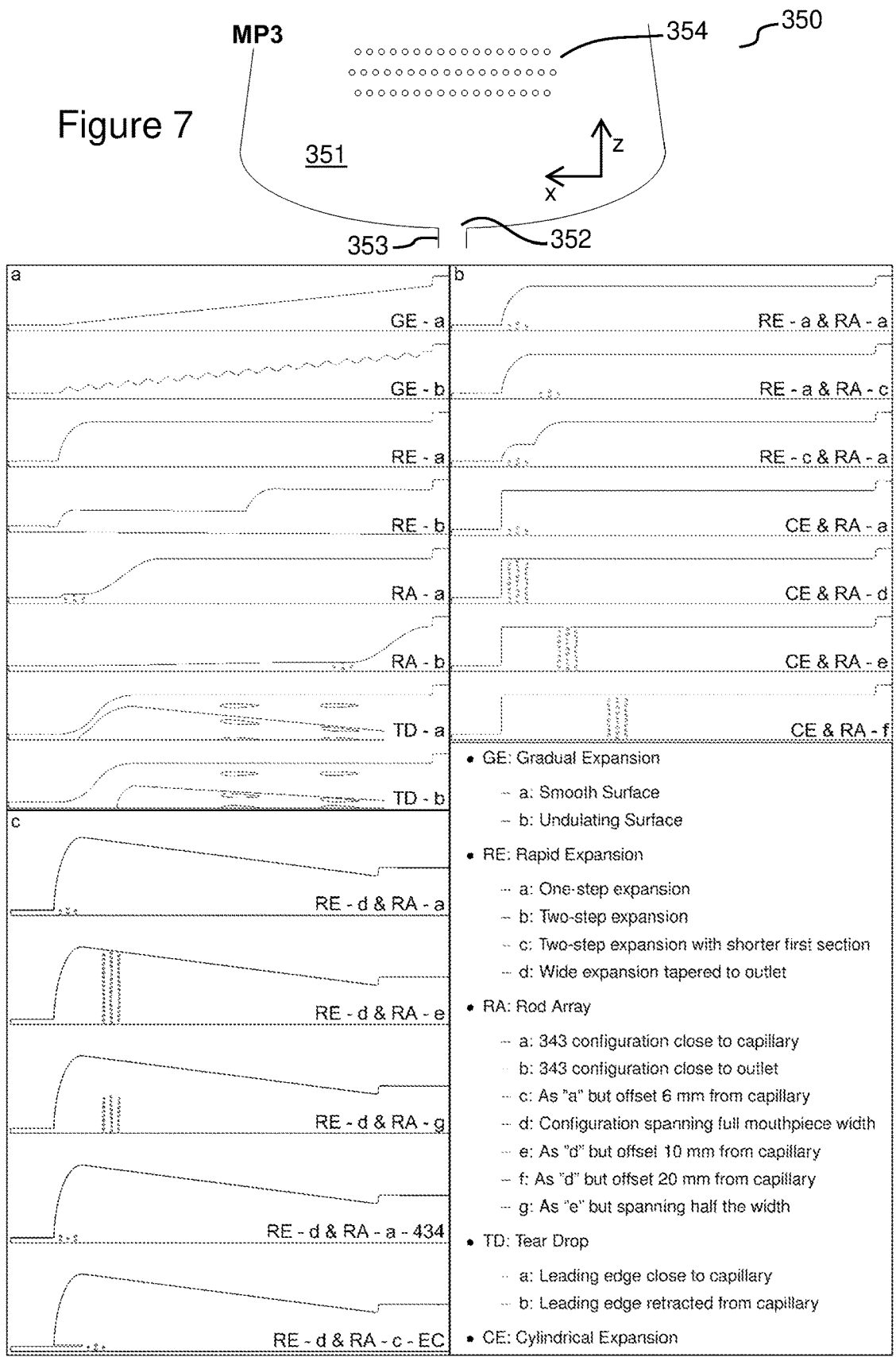
FIG. 7 shows a fifth embodiment of a mouthpiece.
FIG. 8 shows a variety of alternative configurations for jet dispersive elements and sidewall configurations for patient interfaces.

FIG. 7 shows a patient interface 350 which is a mouthpiece (MP). The patient interface 350 provides rapid expansion of the MP wall beginning immediately but not before the outlet orifice 352 of the capillary 353, moving the surfaces available for deposition away from the aerosol and reducing losses. The patient interface 340 comprises a wider rod array 354 that is positioned 10 mm downstream of the capillary to reduce the influence of the rod array 354 deflecting the jet and particles into the nearby walls.

For a child of 12 years old or younger, an approximate mouthpiece size at the mouth interface is 18 mm wide and 13 mm tall. Thus for FIG. 3A, for example, the width w may be 18 mm, and for FIG. 3B, the height h may be 13 mm. For adult DPIs, mouthpiece size may increase to 22×14 mm as with the Twister DPI, 24×15 mm for the Respimat mouthpiece, or 29×12 for a standard nebulizer mouthpiece (Pari eRapid). When a partial rod array, as shown in FIGS. 4A/4B for example, is used in mouthpieces with these dimensions, excessive particle deposition on the mouthpiece walls may occur. To prevent this loss of drug, the mouthpiece should be wider (rapidly expanded) in the vicinity of the rod array in the direction normal (perpendicular) to the length of the rods (FIG. 4A). For a pediatric DPI with a flow rate of 10-20 LPM, this widest dimension should be in the range of 30-40 mm. FIG. 4A depicts the appearance of an exemplary size (also illustrated in the examples) of a maximum width w of 36 mm, which is 2-fold wider than the mouthpiece at the patient interface. This maximum width of 36 mm may need to be increased for higher device flow rates and can potentially be decreased for lower flow rates. As a guide, the example supports the rapid expansion being 36 mm wide and approximately 2-fold the width of the mouthpiece outlet. Based on case study experiments, the mouthpiece height h in the direction of the rod length is less important and can be held at a constant (FIG. 4B) value of e.g. 13 mm, or tapered e.g. from approximately 26 mm at the rods to 13 mm (FIG. 5B). An acceptable range of the mouthpiece heights is 40 to 10 mm.

FIG. 8 illustrates several patient interface alternatives based on an axial cross-section and plane of symmetry. The features include internal geometry control, wall surface characteristics, and internal flow structures, such as the 3D rod array. Wall geometries are intended to either avoid boundary layer separation (gradual expansion) or rapidly move the wall away from the expanding jet (rapid expansion). A rough wall surface is included to improve boundary layer attachment (via boundary layer "tripping"). Internal flow structures are intended to quickly dissipate the turbulent jet with minimal particle depositional loss.

In addition to high efficiency aerosolization and dispersion of the turbulent jet, the air-jet DPI is able to overcome difficulties of delivering aerosol to the lungs of pediatric patients by using positive pressure to aerosolize the powder and inflate the lungs without relying on the child's inspiration. Active devices are often perceived as having the disadvantage of increased complexity and cost due to the requirement for an external gas source. However, significant advantages of positive-pressure devices may include their ability to deliver dry powder aerosol during invasive and non-invasive mechanical ventilation and their ability to administer both the aerosol and a full inhalation breath, which can be beneficial in administering dry powder aerosol to infants. The positive pressure gas source provides highly reproducible actuation of the device, formation of the aerosol and lung delivery of the dose. By contrast, high variability was observed between inhalation waveforms of trained children in a lab setting, which can have a negative effect on the performance of passive DPIs and leads to an unknown amount of dose delivered to the lungs.

Positive pressure air-source device 101 may be an automated air source or a manual air source such as a ventilation bag. In either case the positive pressure air source device 101 actuates the air-jet DPI 102 and provides a full inhalation to the patient. An exemplary automated air source comprises or consists of a pressure regulator, solenoid valve, and microprocessor controlled timer. The automated air source may further comprise a user activated switch such as a push button. Push button actuation of the device provides constant pressure application for a defined time period, resulting in a square waveform flow profile. In embodiments employing a manual air source, an adult can generally generate a 6 kPa pressure source with one hand operation of a small ventilation bag. Given the inhalation volume to be delivered and flow rate specifications, a complete delivery generally occurs start to finish in a matter of seconds, e.g. 1 to 5 seconds, depending in some part on resistance. For instance, for an inhalation volume of 750 ml and a flow rate of 15 LPM (250 ml/s), a full inhalation/delivery takes 3 seconds.

Gas delivery conditions through an exemplary inhaler provide the aerosol and a full inhalation breath to a 5-year-old child. The vital capacity of a 5-year-old child is estimated to be approximately 1 L, which forms the upper limit of the inhaled volume. An exemplary inhaled volume is 75% of this value, or 750 ml. Prior literature has suggested a 500 ml limit, but exceeding this limit was found acceptable considering that it was delivered with positive pressure and not as a result of the child's effort breathing against a resistance. Tracheal gas flow rates for a 5-year-old child are estimated to be ~10 L/min (LPM) at rest and 20 LPM during light exercise. As a result, 10-20 LPM is a suitable exemplary range to use for flows rates for administering the aerosol and inhalation breath.

Intended applications of the pediatric air-jet DPI and DPI system are the delivery of higher dose inhaled medications where efficacy can be increased with improved lung and deep lung targeting, and where reduced inter- and intra-subject variability is important. Potential candidate medications include inhaled antibiotics, growth hormone, anti-virals, gene therapies for lung diseases, bronchodilators and corticosteroids for asthma management, surfactants, clearance agents, insulin, and anti-inflammatories. Expected doses of these medications are in the range of 10-100 mg or more. For example, low dose applications may use approximately 2 mg, whereas high dose applications may use approximately 75 mg dry powder.

EXAMPLES

Example 1. DPI Mouthpieces Reducing Interface and Extrathoracic Depositional Losses Methods CFD models were developed in FLUENT v19.0 (ANSYS Inc., Canonsburg, PA). Briefly, five prismatic near-wall cell layers and an average wall $y^+$ of one was used to resolve the boundary layer flow; the low-Reynolds Number k-w model was implemented to predict the turbulent flow conditions; and a transient form of the transport equations modelled the highly dynamic behavior of the inlet jet. Mesh independence was established using the Roache method [Roache P J: Perspective: A Method for Uniform Reporting of Grid Refinement Studies. *Journal of Fluids Engineering-Transactions of the Asme* 1994, 116:405-413.]. To reduce the time required for evaluation of numerous MP design iterations, correlations were established that relate flow conditions at the outlet of the patient interface to deposition losses in the mouth-throat (MT) region. The correlations were developed by imposing four different velocity profiles, which tested a range of flow characteristics, on the inlet to the MT model and evaluating the difference in ET deposition losses. This example focuses on best-case patient interfaces and describes the aspects of their configuration that diffuse the high-velocity jet and reduce MP and MT depositional losses.

The embodiment of FIG. 3C, referred to as MP1, provides rapid expansion of the MP wall from the capillary, moving the surfaces available for deposition away from the aerosol and reducing losses. However, there is no mechanism in MP1 to diffuse the high-velocity jet, and as such ET losses were not reduced. The embodiment of FIG. 5C, referred to as MP2, uses a similar concept to MP1 but moves the impaction surfaces twice the distance away from the capillary in the radial direction to reduce interface losses further. MP2 also utilizes a 3-4-3 configuration stainless-steel rod array to diffuse the high-velocity jet and reduce downstream aerosol losses. The embodiment of FIG. 7, referred to as MP3, implements a wider rod array that is positioned 10 mm downstream of the capillary to reduce the influence of the rod array deflecting the jet and particles into the nearby walls. Finally, the embodiment of FIG. 6C, referred to as MP4, extends the capillary 6 mm into the interface to both keep the aerosol away from wall surfaces and direct the high-velocity jet through the rods. When evaluating deposition results in the full MP and MT model, each patient interface is coupled to a 5-6 year old MT geometry [Delvadia R, Longest P W, Byron P R: In vitro tests for aerosol deposition. I. Scaling a physical model of the upper airways to predict drug deposition variation in normal humans. *Journal of Aerosol Medicine* 2012, 25:32-40.].

Results and Discussion

Figures 9A, 9B, 9C, 9D, 10:
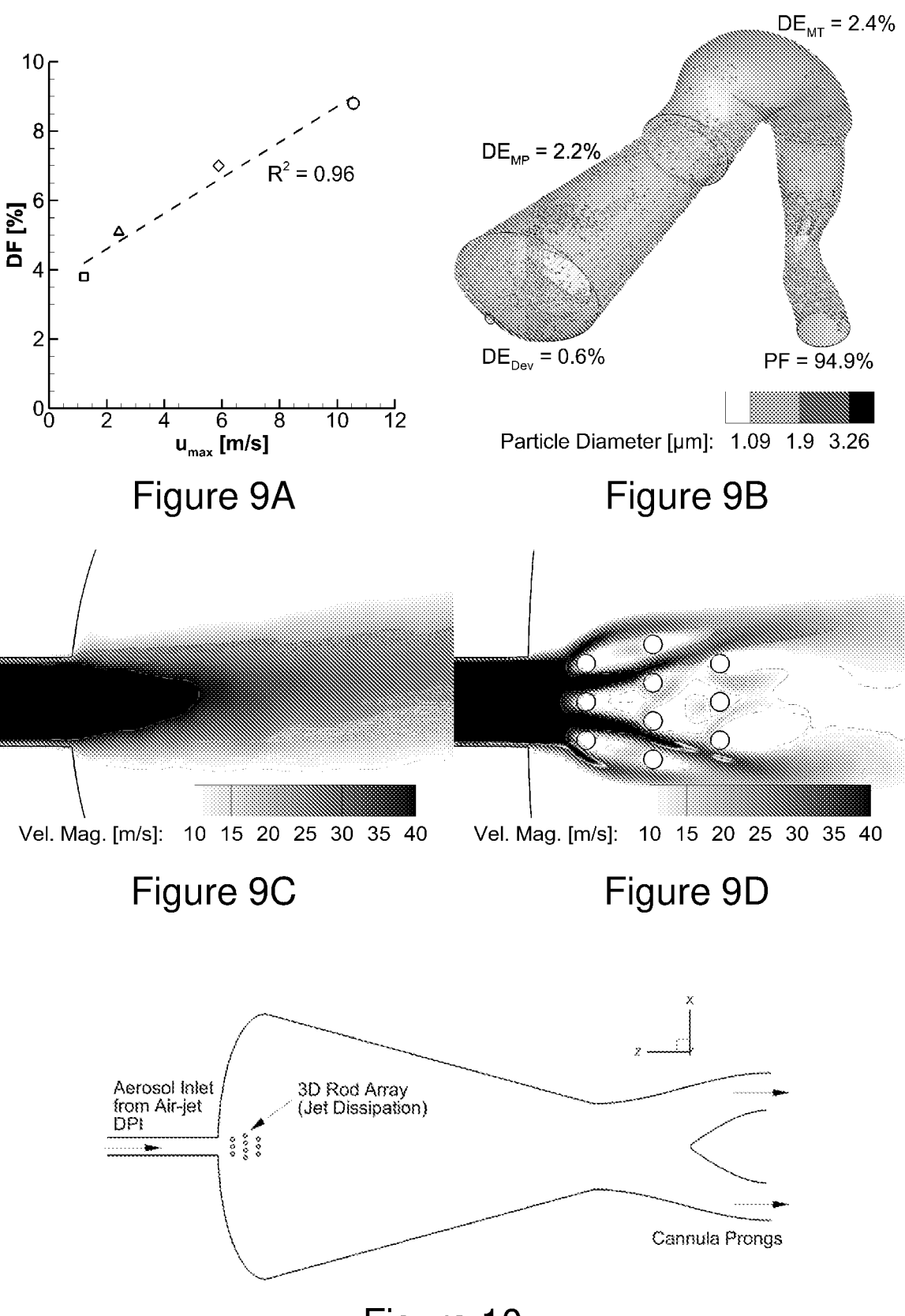
FIG. 9A shows correlation between the peak velocity from the outlet of the mouthpiece and the deposition losses in the extrathoracic (ET) region.
FIG. 9B shows the deposition patterns and regional deposition results for an exemplary mouthpiece.
FIG. 9C shows velocity magnitude contours near a capillary in a patient interface without a 3D rod array.
FIG. 9D shows velocity magnitude contours near a capillary in a patient interface with a 3D rod array.
FIG. 10 shows a top view of a patient interface that includes nasal cannula prongs.

FIG. 9A shows the strong correlation between the peak velocity entering the MT model (from the outlet of the MP) and the deposition losses in the ET region. This linear correlation clearly shows that a high-velocity jet entering the MT from the patient interface leads to higher impaction deposition losses (such as the circle data point in FIG. 9A), and reducing the intensity of the jet can improve system performance by minimizing ET losses (square data point). Therefore, the MP designs that aim to diffuse the high-velocity jet are expected to increase the predicted lung dose based on the CFD models and correlations.

FIG. 9B shows the deposition patterns and regional deposition results in MP4, which demonstrates improvements from expanding the flow passage width near the rod array, extending inlet the capillary, and including a rod array for jet diffusion. The total deposition fraction in the model is low, though it should be noted that the CFD model assumed that particles do not stick to the stainless-steel rods, which is a necessary assumption. Therefore, in vitro testing of the system is expected to result in slightly higher interface losses. That said, the trends predicted by the CFD models show a clear improvement over a MP design with a 15 mm circle at capillary inlet transitioning to a 17×22 mm ellipse at MT interface. Importantly, results in Table 1 indicate that the MP4 design with rod array and rapid expansion compared to MP1 without these features, reduces mouthpiece (MP), mouth-throat (MT) and total depositional loss (shown as deposition efficiency—DE) values by factors of 2.8, 2.0, and 3.0, respectively.

FIGS. 9C and 9D show the velocity magnitude contours near the capillary in MP1 and MP2, which illustrates the effect that the rod array has on the flow field in the patient interface. FIG. 9C clearly shows the high-velocity jet, which the outlet capillary from the DPI generates, entering the MP. Utilizing the rod array, as shown by FIG. 9D, provides effective jet diffusion and reduces the peak flow velocity that enters the downstream ET region, which in turn reduces overall system losses and increases the expected lung dose.

Table 1 summarizes the regional deposition losses, based on CFD calculations, in each of the four MP designs that were identified above. Changing to the rapid expansion geometry in MP1 reduced MT losses, but increased device losses as the design is not streamlined near the capillary, which lead to a marginal improvement in overall depositional losses. Expanding the geometry and including the rod array in MP2 provided a marked improvement in losses in all regions, which reduced the total deposition loss by approximately three-fold. The wider and repositioned rod array in MP3 reduced device losses to less than 1% and maintained the same performance improvements in the other regions. Finally, extending the capillary a short distance into the patient interface in MP4 also gave a device loss of less than 1% and MP and MT losses of approximately 2%, which is consistent with the MP2 and MP3 designs. Both the MP3 and MP4 designs provide similar performance improvements, with the MP4 design preferred as it requires less rods and is therefore easier to manufacture.

TABLE 1

Comparison of evaluated mouth-piece (MP) embodiments compared to the original patient interface showing the CFD-predicted reduction in deposition losses

|  | $DE_{Dev}$ [%] | $DE_{MP}$ [%] | $DE_{MT}$ [%] | $DF_{Tot}$ [%] |
|---|---|---|---|---|
| Original MP | 2.4 | 6.4 | 8.8 | 16.7 |
| MP1 | 5.2 | 6.2 | 4.9 | 15.4 |
| MP2 | 2.6 | 2.0 | 2.2 | 6.6 |
| MP3 | 0.9 | 2.3 | 2.2 | 5.3 |
| MP4 | 0.6 | 2.2 | 2.4 | 5.1 |

MP: Mouth-piece
$DE_{Dev}$: Device deposition efficiency
$DE_{MP}$: Mouth-piece deposition efficiency
$DE_{MT}$: Mouth-throat deposition efficiency
$DE_{Tot}$: Total deposition fraction Conclusion The MP3 and MP4 designs provide CFD-predicted combined patient interface and ET losses of approximately 5%, which combined with the 10% device retention reported by Farkas et al. [Farkas D, Hindle M, Bass K, Longest P W: Development of an Inline Dry Powder Inhaler for Oral or Trans-Nasal Aerosol Administration to Children. *Journal of Aerosol Medicine and Pulmonary Drug Delivery* 2019] provides an expected delivery system and ET loss of 15%, surpassing a desired 75% threshold of loaded dose reaching the lungs. However, a limitation of this example is assumptions by the CFD model do not include deposition loss on the stainless-steel rods or its influence on secondary breakup of the aerosol. In summary, design modifications and utilizing a rod array in our pediatric tobramycin delivery system efficiently diffuses the high-velocity flow generated by the air-jet DPI and reduces patient interface and ET losses by a factor of three-fold. These CFD-based results are experimentally tested and verified in Example 2.

Example 2. Positive Pressure Air-Jet DPI for Pediatric Patients

Methods

Albuterol sulfate (AS) EEG powder was spray-dried using an optimized method [Son Y-J, Longest P W, Hindle M: Aerosolization characteristics of dry powder inhaler formulations for the excipient enhanced growth (EEG) application: Effect of spray drying process conditions on aerosol performance. *International Journal of Pharmaceutics* 2013, 443:137-145.] and the primary particle size of the batch was determined to be 1.2 μm (aerodynamic diameter) using a Sympatec ASPIROS/RODOS dry dispersing unit and HELOS laser diffraction sensor. A pediatric air-jet DPI system consistent with FIGS. 1, 2A, and 2B and their corresponding descriptions was used to both aerosolize the powder and inflate the patient's lungs. For this Example specifically, the device included a vertical aerosolization chamber, inlet flow passage with a diameter of 1.83 mm, and outlet flow passage with a diameter of 2.39 mm connected to a mouthpiece with a 3D rod array made of 0.5 mm diameter rods. The rod array, as shown in FIG. 2A especially the top view inset thereof, was arranged in a 3-4-3 configuration, with the first and last rows containing 3 rods and the middle row (staggered between the openings of the other rows) containing 4 rods. Operating principles behind the air-jet DPI corresponded with the detailed description above. The device was actuated with a positive pressure air volume of 750 mL, supplied from a compressed gas source at 6 kPa, producing a flow rate of 16.3 LPM. The patient interface was a mouthpiece (MP).

To determine device aerosolization performance, a Next Generation Impactor (NGI) was operated at 45 LPM and the device was connected to the NGI inlet using an adapter that allowed the device to operate at 16 LPM with additional makeup air used to achieve the NGI flow rate. To determine lung dose delivery of the system, an in vitro mouth throat (MT) model of a 5-year-old child (Model VTN S, RDD Online) was coated with silicone and modified to accept two filters (SDI Diagnositcs Pulmoguard II, Easton, Massachusetts) connected in series at the MT exit. The MP was designed to be inserted into the MT, with a flange to connect to the exterior of the MT to prevent leaks in the system.

For each experiment, 10 mg of AS-EEG formulation was placed in the aerosolization chamber, then sealed to the underside of the inhaler. Using a solenoid valve and timer, a single actuation containing 750 mL of compressed air was delivered by setting the flow rate and time of valve opening. Drug deposition in the device and either the NGI or MT was determined using accepted High Performance Liquid Chromatography (HPLC) methods with appropriate amounts of deionized water. All results were reported as a percentage of loaded drug dose, with a minimum recovered dose threshold of 90%. Device and MP retention were determined by the amount of drug left in the aerosolization chamber mouthpiece and were used to determine MP emitted dose (ED) by subtracting the two values from the loaded dose. Fine particle fractions (FPF) were reported as a percentage of the drug collected on the impactor stages and these stage mass values were also used to determine the mass median aerodynamic diameter (MMAD). Model losses and filter deposition (lung dose) were given as a percentage of the drug deposited on each with respect to the loaded dose.

Results and Discussion

Drug masses, presented as a percentage of loaded dose, for the inhaler and MP, as well as size characteristics, are given for two different mouthpieces (MP 1 and MP 2) in Table 2. Mouthpiece 1, depicted in FIGS. 3A, 3B, and 3C, comprises a straight extension with an elliptical cross section to fit inside of the MT model and does not include a rod array. Mouthpiece 2, depicted in FIGS. 5A, 5B, and 5C, was configured with a large initial cross-sectional area, to prevent deposition on the walls from the jet leaving the device outlet, then gradually tapers to the smaller cross section to fit inside the MT. Mouthpiece 2 contained a 3D rod array to assist in deaggregation and diffusion of the jet produced by the device outlet. While the results in Table 2 do not show differences in drug retention within the inhaler, both the $FPF_{<5\ \mu m}$ and MMAD values show smaller particles are produced with MP 2. While filter deposition between the two MP designs investigated in this study are similar (66 vs. 68%), MP 2 produced an average MT loss of only 2.5%, which is less than half of MP 1 (6.2%). This difference in MT deposition can be attributed to the smaller particle size exiting MP 2, as well as the diffusion of the outlet jet to prevent particles from entering the MT at a high velocity. Both device configurations tested in this study produced much higher lung delivery efficiency than with previous studies. Because this method does not rely on patient inhalation to achieve high efficiency, it is expected that similar performance would occur in vivo.

TABLE 2

Differences in aerosolization performance between MP 1 (straight elliptical without rod array) and MP 2 (larger initial area gradually decreasing in outlet direction with rod array). Mean aerosol characteristics with standard deviations (SD) shown in parenthesis [n = 3].

| Description | MP 1 | MP 2 |
|---|---|---|
| Device (%) | 12.5 (2.1) | 11.8 (1.6) |
| MP (%) | 7.3 (1.5) | 5.9 (3.1) |
| MP ED (%) | 80.3 (0.9) | 82.3 (1.8) |
| $FPF_{<5\ \mu m/ED}$ (%) | 87.8 (0.8) | 96.8 (1.0) |
| $FPF_{<1\ \mu m/ED}$ (%) | 17.4 (1.2) | 18.6 (1.4) |
| MMAD (μm) | 1.85 (0.06) | 1.67 (0.04) |
| Recovery (%) | 92.6 (1.3) | 92.8 (2.3) |

TABLE 3

Aerosolization and lung delivery efficiency for oral administration through the 5-year-old pediatric MT geometry. Mean aerosol characteristics with standard deviations (SD) shown in parenthesis [n = 3].

| Description | MP 1 | MP 2 |
|---|---|---|
| Device (%) | 14.5 (3.8) | 15.4 (3.0) |
| MP (%) | 9.4 (0.8) | 9.5 (1.4) |
| MP ED (%) | 76.1 (4.5) | 75.1 (1.8) |
| MT Model Loss (%) | 6.2 (0.7) | 2.5 (0.4) |
| Filter (%) | 65.6 (4.0) | 67.8 (0.9) |
| Recovery (%) | 95.7 (1.3) | 95.3 (1.3) |

Conclusions

Results of this Example demonstrate high efficiency in vitro aerosol delivery to a tracheal filter of a pediatric MT model, using a novel positive pressure air-jet DPI design with a 3D rod array. Inclusion of the 3D rod array reduced aerosol size from approximately 1.9 μm to approximately 1.7 μm without a significant increase in MP deposition. Moreover, the 3D rod array reduced the MT depositional loss by a factor of ~2.5-fold. Combining the air-jet and 3D rod array technologies enabled approximately 68% of the loaded dose to reach the tracheal filter. Both positive pressure operation and the small particle size are expected to minimize the observation of intersubject variability with the air-jet DPI.

Example 3. Nose-to-Lung Dry Powder Aerosol Administration to Children with Cystic Fibrosis To demonstrate the advantages of utilizing a rod array to reduce inlet jet intensity into the patient interface and NT region, the current Example compares aerosolization performance in a best-case nasal cannula interface, both with and without a rod array, by using concurrent in vitro testing and CFD analysis. A 3D CAD model rendering of the DPI used for Example 3 is shown in FIG. 2B, and a nasal cannula used in combination with the DPI is shown in FIG. 10. The chosen delivery system employs: nose-to-lung aerosol administration with sufficiently small particles, use of an active positive-pressure (air-jet) DPI, patient interfaces that reduce turbulence and jet momentum effects without substantially increasing particle depositional loss, and highly dispersible spray-dried powder formulations that change size within the airways. The combination of these features maximizes available lung dose in pediatric patients.

Figures 11, 12A, 12B:
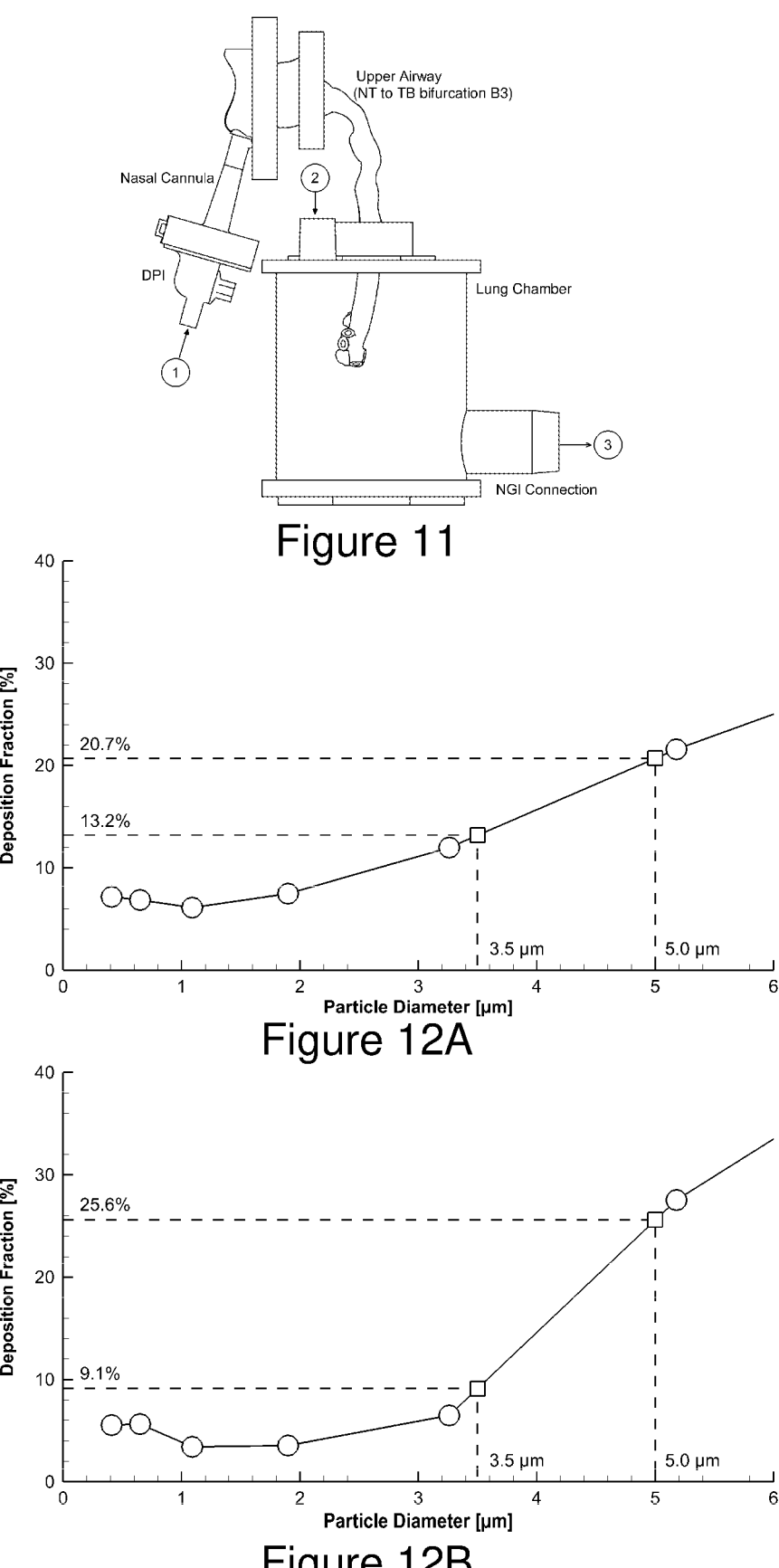
FIG. 11 shows an experimental in vitro lung chamber model for a 5-6-year-old patient.
FIG. 12A shows CFD-predicted deposition profiles in a nasal cannula of a patient interface without a 3D rod array.
FIG. 12B shows CFD-predicted deposition profiles in a nasal cannula of a patient interface with a 3D rod array.

To evaluate upper airway losses and lung delivery efficiency with the chosen delivery system, three realistic airway models of the nose-throat and upper tracheobronchial airways (NT-TB models) were developed for children in the age ranges of 2-3, 5-6, and 9-10 years old. The realistic airway model for the 5-6-year-old patient was physically produced using 3D printing and tested experimentally to provide validation data for the CFD model. All three models were developed in CFD for numerical simulation and prediction of aerosol transport and deposition. Exterior surfaces of the 3D printed NT-TB model and experimental setup are illustrated in FIG. 11. Both the 3D printed model and CFD geometries included a representative lung chamber, which was a cylindrical geometry used to house the TB airways and approximate the particle residence time and thermodynamic conditions (temperature=37° C. and RH=99%) of the lungs. With the in vitro experiment, nasal cannula with and without the rod array were tested in the 5-6 year old model. CFD simulations were considered for all three ages under lung thermodynamic conditions with the rod array nasal interface.

The airway geometries used in the in vitro and numerical models consists of an upper airway (NT to TB bifurcation B3) extracted from CT scans and a lung chamber that was designed to provide an aerosol residence time of approximately two seconds throughout the entire model (again, see FIG. 11). Characteristic airway dimensions for the three upper airway models are provided in Table 4.

TABLE 4

Characteristic dimensions for the 2-3-, 5-6-, and 9-10-year old upper airway models.

| Dimension | 2-3-year-old | 5-6-year-old | 9-10-year-old |
|---|---|---|---|
| V [mm$^3$] | 18,411 | 24,186 | 41,323 |
| $A_s$ [mm$^2$] | 13,742 | 16,202 | 23,060 |
| $V/A_s$ [mm] | 1.34 | 1.49 | 1.79 |
| $L_{CP}$ [mm] | 124.4 | 126.4 | 128.5 |
| $\sqrt{V/L_{CP}}$ [mm] | 12.2 | 13.8 | 17.9 |
| $D_{h,\ G}$ [mm] | 5.7 | 6.7 | 6.8 |
| $L_T$ [mm] | 64.6 | 75.3 | 97.7 |

V: NT-B3 volume
$A_s$: NT-B3 surface area
$L_{CP}$: Central path length from nostrils to glottis
$D_{h,\ G}$: Hydraulic diameter of the glottis
$L_T$: Length of trachea from glottis to carinal ridge For the in vitro experiment, multiple batches of a spray-dried albuterol sulfate (AS) enhanced excipient growth (EEG) powder formulation were produced based on the optimized method described by Son et al. (2013) using a Büchi Nano spray dryer B-90 HP (Büchi Laboratory-Techniques, Flawil, Switzerland). The AS EEG powder formulation contained a 30:48:20:2% w/w ratio of AS, mannitol, 1-leucine, and Poloxamer 188. The AS EEG powder was used as a model test spray dried formulation in place of antibiotic EEG formulations (e.g tobramycin). It is expected that antibiotic EEG powder formulations with the same hygroscopic properties as the AS EEG formulation will perform comparably in regard to targeted lung delivery.

The device actuation and experimental testing will now be briefly summarized. The DPI aerosolization chamber is loaded with 10 mg of AS EEG powder and actuated with a 6 kPa positive-pressure air source, using a compressed air line and solenoid valve device, which efficiently aerosolizes the powder. Characterization of the aerosol that leaves the growth chamber was performed using a Next-Generation Impactor (NGI) and AS drug masses were assayed with high-performance liquid chromatography (HPLC). All recovered doses from experimental runs were greater than 90% (average of 96.5%).

The device emitted dose (ED) was defined as the difference between the loaded AS dose and the mass of AS retained in the DPI after actuation, divided by the loaded dose, and expressed as a percentage. The delivery system ED was defined with a similar method, with the mass of AS retained in the DPI and nasal cannula divided by loaded dose. The aerosol MMAD was identified with linear interpolation of a cumulative percentage drug mass vs. cut-off diameter plot from the NGI. The cut-off diameters of each NGI stage were calculated using the formula specified in USP 35 (Chapter 601, Apparatus 5) for the operating flow rate of 45 LPM. T-tests were used with JMP-Pro® 12 (SAS Institute, Cary, NC) for statistical analysis. The p-value $<0.05$ was considered as significant.

Results

Table 5 compares the experimentally determined aerosolization performance of delivery systems that employ a nasal cannula both with and without a rod array. These results show no statistical significance between the two cannula designs in terms of DPI retention or cannula emitted dose (p-value of 0.21 and 0.08, respectively). However, the cannula retention and particle size (as MMAD) is significantly lower for the device that does utilize a rod array for jet attenuation (p-values of 0.01 and $<0.001$, respectively). This demonstrates that the reducing the intensity of the inlet jet that enters the patient interface reduces losses in the cannula, and hence maximizes available lung dose to the patient. Furthermore, the rods provide secondary powder break-up mechanisms that reduce the aerosol size, which in turn improves delivery through the nose.

TABLE 5

Experimentally determined aerosolization performance of the dry powder inhaler and nasal cannula delivery system both with and without a rod array utilized in the patient interface.

| | Nasal Cannula without Rod Array | Nasal Cannula with Rod Array |
|---|---|---|
| DPI Retention [%] | 17.4 (1.2) | 18.2 (0.9) |
| Cannula Retention [%] | 8.9 (0.3) | 6.0 (1.0)* |
| Cannula Emitted [%] | 73.7 (0.9) | 75.9 (1.8) |
| MMAD [μm] | 1.94 (0.03) | 1.67 (0.02)* |
| Recovered [%] | 97.1 (3.0) | 97.6 (1.3) |
| $FPF_{<5 \ \mu m}$ [%] | 85.4 (0.3) | 95.5 (0.7)* |
| $FPF_{<1 \ \mu m}$ [%] | 15.7 (0.6) | 18.7 (0.5) |

MMAD: Mass-median aerodynamic diameter

FPF: Fine particle fraction

*P < 0.05; paired t-test; significant improvement in aerosolization performance with implementation of 3D rod array The CFD-predicted flow field and particle deposition patterns in the nasal cannulas showed good validation against the experimental testing, with CFD-predictions of losses in the patient interface falling within the experimental SD in both cases. The high-velocity jet extends into the cannula up to approximately the cannula bifurcation in the case of no 3D rod array. By contrast the jet is completely dissipated by approximately 25% of the cannula length with the 3D rod array. Furthermore, the deposition pattern without rods shows that particles in the 1-5 μm range, which accounts for the bulk of the aerosol size distribution, readily deposit on the cannula bifurcation and prongs. Conversely, the model with rods shows less deposition of particles in the 1-5 μm range in these regions, with only the smaller (<1 μm) particles (which account for much less aerosol mass) being lost in the patient interface walls due to more secondary flow induced by the rod array.

Maximizing delivery to pediatric CF patient is further facilitated by use of appropriately sized aerosols, and aerosol size is affected by the presence and configuration of a 3D rod array in the patient interface. FIGS. 12A and 12B show CFD-predicted deposition profiles (deposition fraction vs. aerodynamic particle diameter) in the nasal cannula both without rods (FIG. 12A) and with rods (FIG. 12B). The plot labels points at an MMAD of 3.5 μm and 5.0 μm (consistent with sizes typical of adult commercial DPIs) which lead to an approximate 2- to 5-fold increase in patient interface losses over the pediatric air-jet DPI presented in this Example. Furthermore, the small particle size (1.67 μm (0.02 μm) MMAD) that was achieved with utilization of the rod array in this nasal cannula is expected to maximize nasal transmission downstream of the patient interface. In summary, appropriately sized particles and the aerosolization performance of the pediatric air-jet DPI with rod-array nasal cannula can produce high efficiency lung delivery of the aerosol.

CFD predictions of NT-TB (through B3) depositional loss showed good agreement with the experimental predictions and low extrathoracic and upper airway loss of the aerosol. Considering the 5-6 year-old NT-TB model, CFD predicted depositional loss was 4.8%, which fell within the standard deviation (SD) range of the experimental mean (SD) value of 6.6% (2.6%). CFD predicted NT-TB depositional loss across the age ranges of 2-3, 5-6 and 9-10 years old were 10.9%, 4.8% and 7.0%, respectively. As a result, extrathoracic and upper airway loss of the aerosol was approximately 11% or below for this highly challenging delivery scenario. CFD predictions of aerosol size increase in the lung chamber under humid airway conditions indicated an outlet size of approximately 3.4 to 3.5 μm due to hygroscopic growth of the EEG aerosol, which was significantly larger than the initial 1.67 μm aerosol entering the nose.

Discussion

This Example demonstrates an embodiment that overcomes the primary limitations associated with dry powder aerosol administration to children and enables high efficiency trans-nasal DPI use in this population, based on concurrent CFD and realistic in vitro analysis. Techniques used to improve lung delivery efficiency of the dry powder aerosol included nose-to-lung administration in subjects as young as 2-years-old, use of a positive-pressure active DPI, implementation of patient interfaces that improved aerosol deaggregation and dissipation of the flow field, and controlled condensational growth of the aerosol within the airways. Resulting upper airway losses of 11% and below provide a vast improvement to lung doses in pediatric patients compared to commercial devices. The validated CFD models showed the aerosol MMAD is expected to grow to a range of 3.4 to 3.5 μm in the lower airways after a residence time of approximately 0.6 seconds. Results showed differences in NT-B3 losses between the three models, which are attributed to differences in airway dimensions between patients at different ages (see Table 1) and perhaps intersubject variability within each age group.

Comparisons made between the experimentally-tested and CFD-predicted performance of the nasal cannula, both with and without rods, demonstrated that utilizing a rod array in the patient interface can both minimize losses in the patient interface and reduce the aerosol size that enters the NT region. This small particle size reduces impaction deposition losses in the nasal cavity, as demonstrated by the small (approximately 5%) upper airway loss from the 5-6-year-old NT-TB model. Finally, the highly-dispersible spray-dried EEG powder, which grew to an MMAD of 3.4 to 3.5 μm after a 0.6 sec residence time, is expected to target delivery in the lower airways, where bacterial infection is more difficult to eradicate.

It is to be understood that the terminology used herein is for the purpose of describing particular embodiments only, and is not intended to be limiting, since the scope of the present invention will be limited only by the appended claims.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be separated from or combined with the features of any of the other several embodiments without departing from the scope or spirit of the present invention. Any recited method can be carried out in the order of events recited or in any other order which is logically possible.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described.

What is claimed is:

1. A device for patient interfacing and administration of an aerosol to be delivered to the lungs, comprising
a lumen with one or more exit orifices leading to a recipient;

a 3D rod array arranged in the lumen, wherein the 3D rod array comprises a plurality of rows, wherein each row has a plurality of unidirectional rods which extend between opposite walls of the lumen, wherein the plurality of rows are spaced apart from one another along a primary flow axis of the lumen such that the rods do not contact one another;
a capillary configured to pass a flow of drug aerosol; and
at least one drug aerosol inlet orifice for delivering a drug aerosol air jet from the capillary to the lumen,
wherein proximity of the drug aerosol inlet orifice to a first row of the 3D rod array is such that the drug aerosol air jet from the capillary is forced to flow through the 3D rod array, and
wherein at least one cross-sectional dimension of the lumen is increased relative to the diameter of the at least one drug aerosol inlet orifice, wherein the increase in the at least one cross-sectional dimension begins at or before the at least one drug aerosol inlet orifice, wherein the at least one cross-sectional dimension of the lumen is oriented perpendicular to a long axis of the rods of the 3D rod array.

2. The device of claim 1, wherein the 3D rod array spans an entire cross-sectional distance of the lumen between the at least one drug aerosol inlet orifice and the one or more exit orifices in a direction perpendicular to a long axis of the rods of the 3D rod array.

3. The device of claim 1, wherein the 3D rod array spans less than an entire cross-sectional distance of the lumen between the at least one drug aerosol inlet orifice and the one or more exit orifices in a direction perpendicular to a long axis of the rods of the 3D rod array.

4. The device of claim 3, wherein at least one gap between a wall of the lumen and a rod of the 3D rod array nearest the wall exceeds a maximum distance between any two adjacent rods.

5. The device of claim 3, wherein the 3D rod array is spaced 0 to 5 mm away from the at least one drug aerosol inlet orifice along a primary flow axis of the lumen.

6. The device of claim 5, wherein the 3D rod array is spaced 1 to 2 mm away from the at least one drug aerosol inlet along the primary flow axis of the lumen.

7. The device of claim 3, wherein the at least one cross-sectional dimension of the lumen increases along a long axis of the lumen in a direction away from the at least one drug aerosol inlet orifice for a length of the long axis corresponding in position with the 3D rod array.

8. The device of claim 7, wherein the increase is gradual or instantaneous.

9. The device of claim 7, wherein a widest dimension is in the range of 30-40 mm for a pediatric DPI flow rate of 10-20 LPM.

10. The device of claim 1, wherein the at least one inlet comprises a flow passage that projects a non-zero distance into the lumen from one end of the lumen opposite the one or more exit orifices before admitting the air jet to the lumen.

11. The device of claim 1, wherein the device is a patient interface.

12. The device of claim 11, wherein the patient interface is a mouthpiece.

13. The device of claim 11, wherein the patient interface comprises one or more nasal prongs.

14. An air jet dry powder inhaler (DPI) system, comprising
an air jet DPI, comprising
a fixed position elongate aerosolization chamber with a longitudinal axis, one or more inlets for forming at least one cross flow air jet with an air jet axis, wherein the air jet axis is at a non-zero angle with the longitudinal axis of the aerosolization chamber, wherein the one or more inlets are flow passages or first orifices, and one or more outlets leading off the aerosolization chamber, wherein the one or more outlets are flow passages or second orifices; and a patient interface, comprising a lumen with one or more exit orifices, a 3D rod array arranged in the lumen, wherein the 3D rod array comprises a plurality of rows, wherein each row has a plurality of unidirectional rods which extend between opposite walls of the lumen, wherein the plurality of rows are spaced apart from one another along a primary flow axis of the lumen such that the rods do not contact one another, a capillary configured to pass a flow of drug aerosol from the aerosolization chamber toward the lumen, and at least one drug aerosol inlet orifice for delivering a drug aerosol air jet from the capillary to the lumen, wherein proximity of the drug aerosol inlet orifice to a first row of the 3D rod array is such that the drug aerosol air jet from the capillary is forced to flow through the 3D rod array, and wherein at least one cross-sectional dimension of the lumen is increased relative to the diameter of the at least one drug aerosol inlet orifice, wherein the increase in the at least one cross-sectional dimension begins at or before the at least one drug aerosol inlet orifice, wherein the at least one cross-sectional dimension of the lumen is oriented perpendicular to a long axis of the rods of the 3D rod array.

15. The air jet DPI system of claim 14, further comprising a positive pressure air source for actively supplying a complete inhalation volume to a patient.

16. The air jet DPI system of claim 14, wherein the 3D rod array spans an entire cross-sectional area of the lumen between the at least one drug aerosol inlet orifice and the one or more exit orifices.

17. The air jet DPI system of claim 14, wherein the 3D rod array spans less than an entire cross-sectional distance length of the lumen between the at least one drug aerosol inlet orifice and the one or more exit orifices in a direction perpendicular to a long axis of the rods of the 3D rod array.

18. The air jet DPI system of claim 17, wherein at least one gap between a wall of the lumen and a rod of the 3D rod array nearest the wall exceeds a maximum distance between any two adjacent rods.

19. The air jet DPI system of claim 17, wherein the 3D rod array is spaced 0 to 5 mm away from the at least one inlet orifice along a primary flow axis of the lumen.

20. The air jet DPI system of claim 19, wherein the 3D rod array is spaced 1 to 2 mm away from the at least one inlet along the primary flow axis of the lumen.

21. The air jet DPI system of claim 17, wherein the at least one cross-sectional dimension of the lumen increases along a long axis of the lumen in a direction away from the at least one drug aerosol inlet orifice for a length of the long axis corresponding in position with the 3D rod array.

22. The air jet DPI system of claim 21, wherein the increase is gradual or instantaneous.

23. The air jet DPI system of claim 21, wherein a widest dimension is in the range of 30-40 mm for a pediatric DPI flow rate of 10-20 LPM.

24. The air jet DPI system of claim 14, wherein the at least one inlet comprises a flow passage that projects a non-zero distance into the lumen from one end of the lumen opposite the one or more exit orifices before admitting the air jet to the lumen.

25. The air jet DPI system of claim 14, wherein the patient interface comprises one or more nasal prongs.

\* \* \* \* \*